(12) United States Patent
Segal

(10) Patent No.: US 6,500,000 B1
(45) Date of Patent: Dec. 31, 2002

(54) HANDPIECE FOR A DENTAL SYRINGE ASSEMBLY

(76) Inventor: Alan Julian Segal, 13 Park Avenue, Hale, Cheshire (GB), WA 15 9DL ( * ) Notice: Subject to any disclaimer, the term of this patent is extended or adjusted under 35 U.S.C. 154(b) by 0 days.

(21) Appl. No.: 09/868,265

(22) PCT Filed: Dec. 17, 1999

(86) PCT No.: PCT/GB99/04201

§ 371 (c)(1),
(2), (4) Date: Jul. 30, 2001

(87) PCT Pub. No.: WO00/35370

PCT Pub. Date: Jun. 22, 2000

(30) Foreign Application Priority Data

Dec. 17, 1999 (GB) ................................. 9827716

(51) Int. Cl.⁷ ............................................. A61C 17/02
(52) U.S. Cl. ............................................ 433/80; 433/85
(58) Field of Search ............................. 433/80, 84, 81, 433/85, 88; 604/244

(56) References Cited

U.S. PATENT DOCUMENTS 4,149,315 A    4/1979  Page
4,531,913 A  * 7/1985  Taguchi ........................ 433/80
4,619,612 A  * 10/1986 Weber et al. ................... 433/80
5,908,296 A  * 6/1999  Kipke et al. ................... 433/80
5,944,520 A  * 8/1999  Ash ............................. 433/84
2001/0041321 A1  11/2001 Segal

FOREIGN PATENT DOCUMENTS

| EP | 0 365 300 A | 4/1990 |
| WO | WO 90/07912 | 7/1990 |
| WO | WO 98 57597 A | 12/1998 |
| WO | WO 98/57597 | 12/1998 |

* cited by examiner

*Primary Examiner*—Cary E. O'Connor
(74) *Attorney, Agent, or Firm*—Hollander Law Firm, P.L.C.

(57) ABSTRACT

A dental syringe assembly has a handpiece connected to air and water lines and a tip for directing air and water flow into a patient's mouth. The tip has an enlarged cap that is detachably engageable with a sleeve structure of a head member of the handpiece. The sleeve structure may be provided in a connection piece that fits within a socket in the head member so that the connection piece can rotate but is retained against removal. A non-return valve may be provided within the head member to prevent return flow of contaminated water.

24 Claims, 3 Drawing Sheets

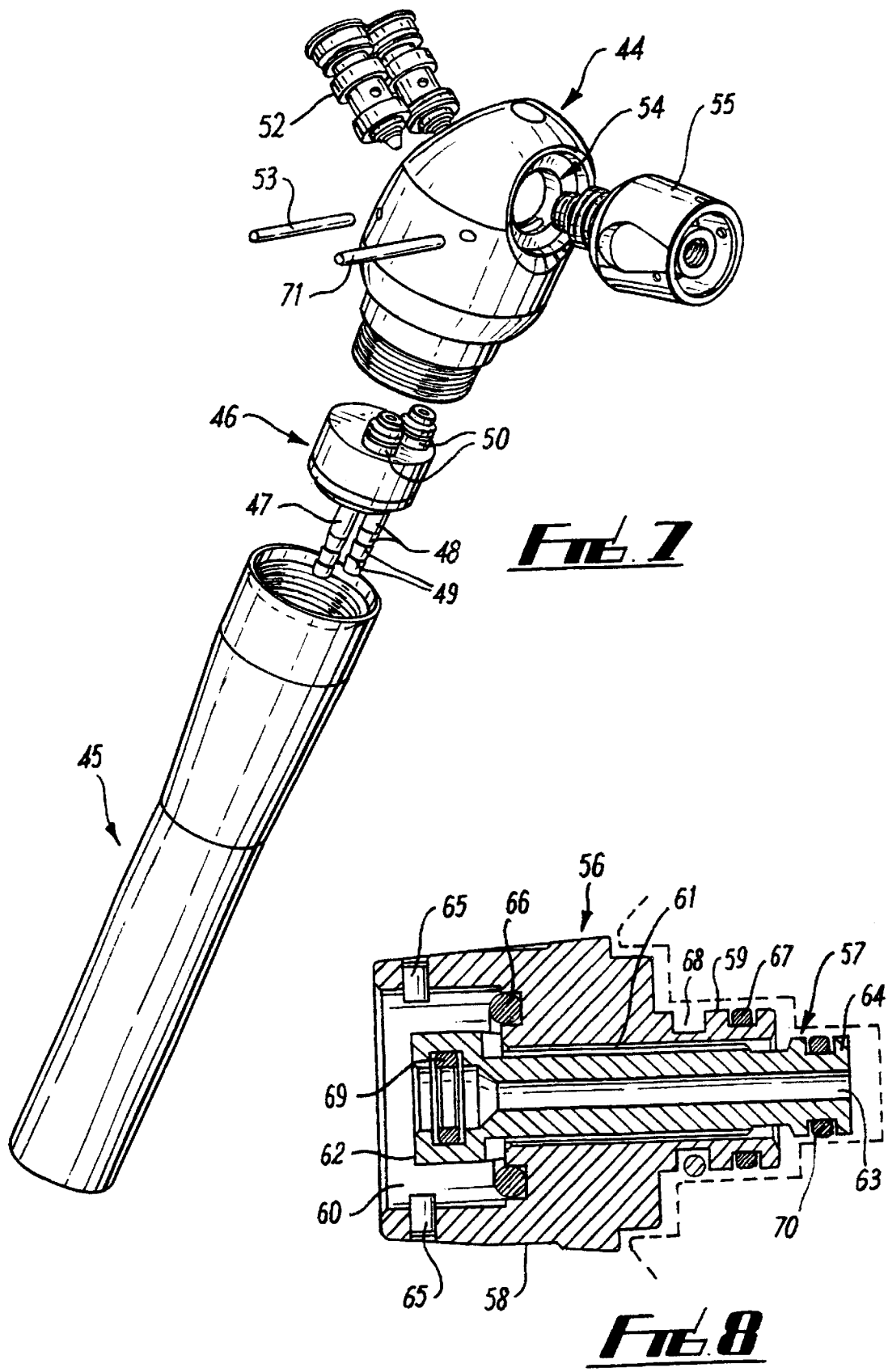

HANDPIECE FOR A DENTAL SYRINGE ASSEMBLY

TECHNICAL FIELD

This invention relates to dental syringe assemblies such as are used by dentists to direct air and/or water into a patients mouth for cleansing and drying purposes.

BACKGROUND ART

An assembly of this kind is described in prior patent specification WO 90/07912. The assembly described has a disposable plastics syringe tip which is connected via an adaptor to a handpiece body to which air and water are supplied. The tip can be discarded after use to avoid spread of infection between patients. The adaptor is selected for the particular handpiece body to permit use of a tip having a standardised connection. It is also possible to connect a disposable plastics syringe tip directly (i.e. without an adaptor) to a dedicated handpiece body.

Whilst this known arrangement provides an effective means of preventing transfer of infection via material retained within the tip, there is the possibility of infected material from one patient gaining access beyond the tip to the handpiece body or adaptor from where it can be passed on to the next patient through a fresh tip.

With a view to overcoming this problem, prior application PCT/GB 98/01754 proposes the provision of a non-return valve between the tip and the hand-piece body. This can prevent flow-back of infected material but, in the case where the valve is provided in the handpiece body there is the-problem of conveniently sterilising the valve itself.

An object of the present invention is to provide an improved handpiece having means to avoid transfer of infection due to access of infected material beyond the tip and which is convenient to sterilise.

DISCLOSURE OF THE INVENTION

According to one aspect of the invention therefore there is provided a handpiece for a dental syringe assembly adapted to be connected on the one hand to sources of air and water, and on the other hand to a tip for directing flow of air and water from the handpiece into a patient's mouth, characterised in that the handpiece is comprised of at least two releasably connectable members, and wherein one of said handpiece members has a non-return valve incorporated therein.

With this arrangement, the valve can help prevent draw back along the tip from the open end thereof of contaminated fluids and can also block access of infected material beyond the tip and thereby prevent transmission of infection between patients.

In addition, in so far as the handpiece members are separable cleansing and sterilisation can be effected in a particularly convenient manner, a consideration which is of upmost importance when providing instruments for dental treatment.

The separable members of the handpiece may comprise a head member which is adapted to be connected to the tip and a body member which is adapted to be connected to the air and water sources, the head member incorporating the non-return valve.

The body member may house a coupling or connecting member with conduits to channel the flow of air and water through the body to the head member. The conduits may be provided with shut off valves.

The body member may comprise a tubular structure which is screwed or otherwise releasably engaged relative to the head member. Where the aforesaid connecting member is provided the head member may be held in detachable engagement with the connecting member by the said releasable engagement of the tubular structure with the head member.

In the case where the syringe assembly is arranged for separate delivery of air and water, the non-return valve is preferably applied to the water delivery, although alternatively or additionally, the valve may be applied to the air delivery.

In a particularly preferred embodiment, the tip has separate air and water passages which may be arranged coaxially or alongside each other and these are connected separately to air and water inlets at the handpiece body, and in this case the non return valve is preferably applied to the water passage only.

The non-return valve may be of any suitable form. In a preferred embodiment, the valve has a spring loaded valve member, such as a ball, which is urged into sealing engagement with a valve seat, fluid pressure during normal operation being sufficient to move the member off the seat to permit passage of fluid.

Other kinds of non-return valve can also be used. For example, in an alternative embodiment, the valve is of the constriction kind whereby valve parts, such as silicon rubber reeds, tend to collapse or are urged into sealing contact with each other but move apart in normal operation to permit passage of fluid.

In the case where the valve is applied to water delivery which is separated from air delivery, the valve may incorporate an outlet flow nozzle to direct flow into the water passage of the tip and help prevent communication, and hence transfer of material, between the air and water passages.

This nozzle may be such as to extend into the water passage of the tip and help form a seal therewith. The nozzle may be tapered to form a tight wedging fit within the tip passage and this may contribute to or establish a seal. Alternatively or additionally there may be an O-ring seal or other sealing arrangement to fit around the tip passage, for example an O-ring seal concentrically around the said nozzle whereby a tubular part of the tip defining an inlet to the water passage fits tightly between the nozzle and the O-ring seal.

As described in the above mentioned prior patent specification, the tip may be disposable and the handpiece may be adapted for detachable engagement for use with a standardised tip directly or via an adapter.

The handpiece may be adapted for detachable engagement with the tip via a bayonet connection, although other connections may also be used.

In a particularly preferred embodiment the handpiece incorporates a sleeve structure for detachable engagement with the tip, preferably via the aforesaid bayonet connection, and this sleeve structure preferably incorporates the said non-return valve and preferably also is incorporated in the aforesaid head member.

This sleeve structure may be located in a bore in the handpiece so as to be movable axially inwardly of the handpiece against the action of a spring to facilitate the aforesaid detachable interengagement. The sleeve structure, and hence the tip when connected thereto, may be rotatable when the sleeve structure is spring urged to an outer limit position whereas rotation may be resisted when the sleeve structure is pushed against the spring to an inner limit position. An appropriate toothed clutch or other mechanism or device may be provided to achieve this resistance. The resistance to rotation enables interengagement and disengagement of the tip and sleeve structure whilst free rotation, preferably through 360°, facilitates easy use of the tip. Connections of air and water to the tip preferably occur via the sleeve structure preferably such as to maintain flow during such rotation.

The above described sleeve structure advantageously provides a convenient means of attachment of a tip of the kind having a connection cap direct to a handpiece preferably using a bayonet connection.

Thus and in accordance with a further aspect of the present invention there is provided a dental syringe assembly comprising a handpiece adapted to be connected to sources of air and water and a tip for directing flow of air and water from the handpiece into a patients mouth, the tip having an enlarged connector cap at a rear end, and the handpiece having a body member and a head member, characterised in that the head member is provided with a sleeve structure and the connector cap of the tip is detachably interengageable with the sleeve structure.

Other aspects of the sleeve structure and the tip may be as described above.

The head member may be connected to the body member so as to be separable therefrom.

Preferably, the body member comprise a tubular structure which is releasably connected to the head member. Preferably also the body member houses a tubular structure which is releasably connected to the head member.

In a particularly preferred embodiment, the said sleeve structure is provided in a connection piece attached to the head member.

Preferably, the tip has inner and outer coaxial passages for the water and air flow and the said sleeve structure comprises a central inner bore to communicate with the inner coaxial passage within the cap, and an outer passageway defined by a recess around the inner bore to communicate with the outer coaxial passage within the cap.

Preferably also, the connection piece is attached to the head member within a socket of the head member, whereby air and water passageways in the head member are in sealed communication respectively with air and water passageways on the connection piece.

The connection piece preferably has a head part which projects externally of the head member of the handpiece, the sleeve structure being provided exclusively within this head part.

Further, the connection piece is preferably located within the socket so as to be rotatable about its axis whilst being retained against axial separation. The connection piece may be retained by a transverse assembly pin passed through the head member and engaging a peripheral groove in the connection piece.

BRIEF DESCRIPTION OF THE DRAWINGS

The invention will now be described further by way of example only and with reference to the accompanying drawings in which:

FIGS. 7 & 8 are respectively an exploded perspective view and a sectional view of a part of a handpiece in accordance with an alternative embodiment.

Referring to FIG. 1, this shows a handpiece having a tubular cylindrical body 1 and a head 2.

Figure 1:
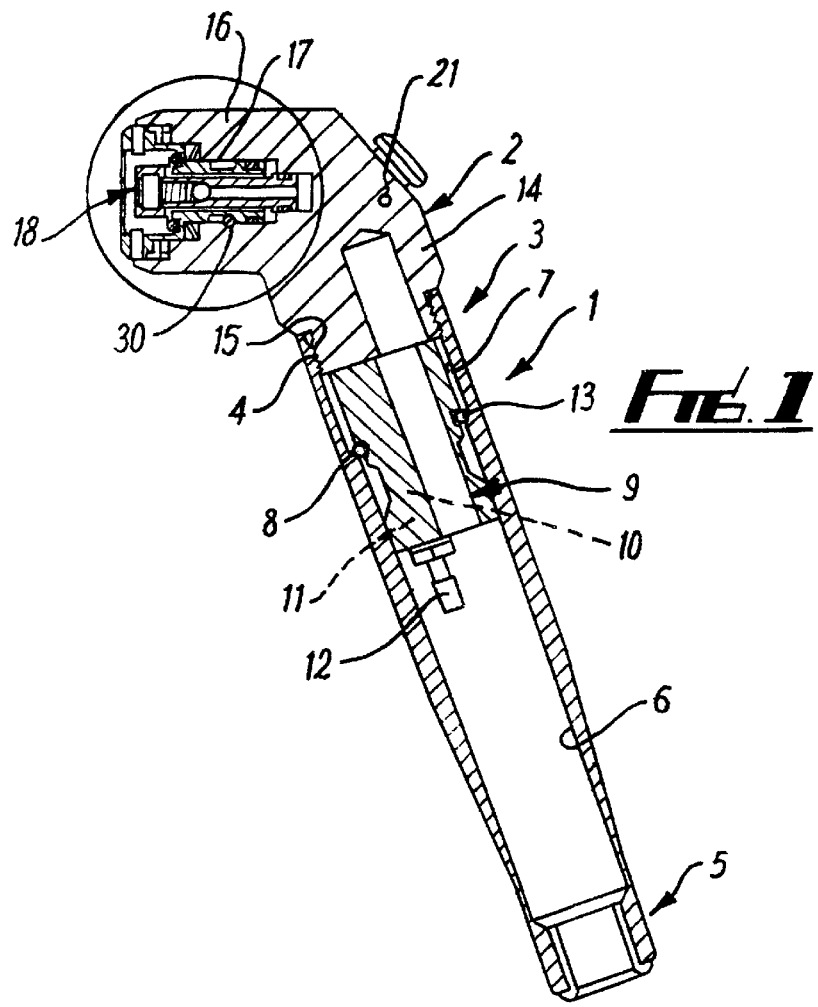
FIG. 1 is an axial sectional view of one form of a handpiece according to the invention.

The tubular body 1 has an open forward end 3 with an inner screw thread 4, and an open rearward end 5 in the form of a narrowed neck. Between the screwthread 4 and the neck 5 the body 1 has a cylindrical inner surface which has a main section 6 which is of the same diameter throughout and a short end section 7 adjacent the screwthread 4 which has a larger diameter. A peripheral internal shoulder 8 is established between this larger diameter end section 7 and the adjacent main section 6.

Within the tubular body 1 adjacent to the open forward end 3 there is a generally cylindrical coupling member 9 (apertured for weight reduction) which has two conduits 10, 11 extending therethrough. These conduits are open at a forward end of the member 9. At a rearward end, the two conduits 10, 11 have projecting line connectors 12 (only one of which is shown). Pressurised air and water lines (not shown) enter the body 1 through the neck 5; the air line is connected to one of the conduits 10 via one of the line connectors 12 and the water line is connected to the other conduit 11 via the other connector 12.

The member 9 has a rearward end section which is a close fit within the main section 6 of the body. The member 9 has a waisted central section and at the side of this facing towards the forward end there is a peripheral ring 13 set in a retaining groove. This ring 13 engages the shoulder 8 to restrict movement of the member 9 along the body 1 towards the rearward end.

Figure 2:
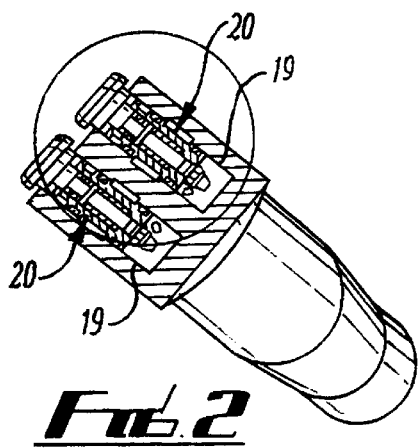
FIG. 2 is a part sectioned top view of the handpiece.
Figure 4:
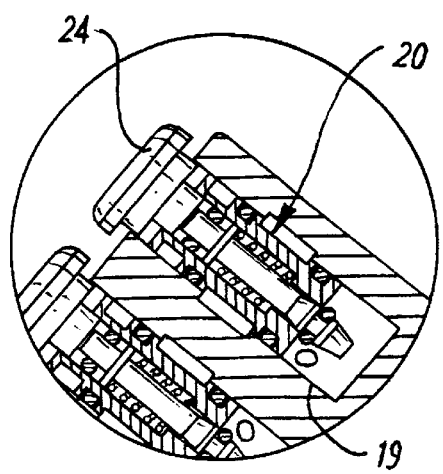

The head 2 is an angular body having a rearward part 14 terminating in a neck section with an external screwthread 15 and a forward part 16 with an axial recess 17 receiving a combined tip connector and one way valve mechanism 18 described later. There are also two side recesses 19 (FIG. 2) which receive push-button control valves 20 held in position relative to the head 2 by an assembly pin 21 (FIG. 1) pushed transversely through the head 2.

The head 2 contains air and water conduits which run between openings at the rearward end and cavities 22, 23 (FIG. 3) within the recess 17, via the control-valve recesses 19.

The head 2 can be screwed into the end of the body 1 on top of the member 9 until a limit position is reached at which the ring 13 on the member 9 is firmly pressed against the shoulder 8. In this position the air and water conduit openings in the forward end of the member 9 are aligned with the air and water conduit openings in the rearward end of the head 2.

The control valves 20 are of conventional form and permit flow of air and/or water from the air and water lines through the conduits in the member 9 and the head 2 to the tip connector and valve mechanism 18, in dependence on the activation of the press buttons 24.

Figure 5:
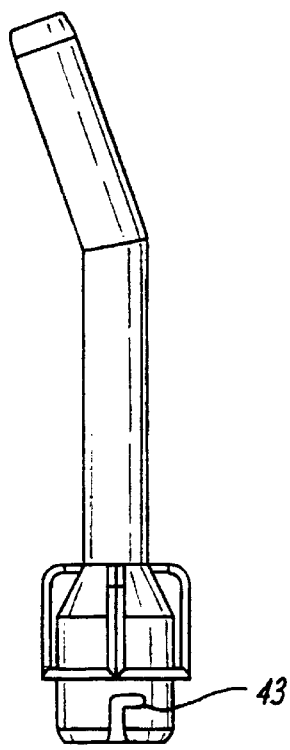
FIGS. 5 & 6 are side and axial section views of a tip used with the handpiece.
Figure 6:
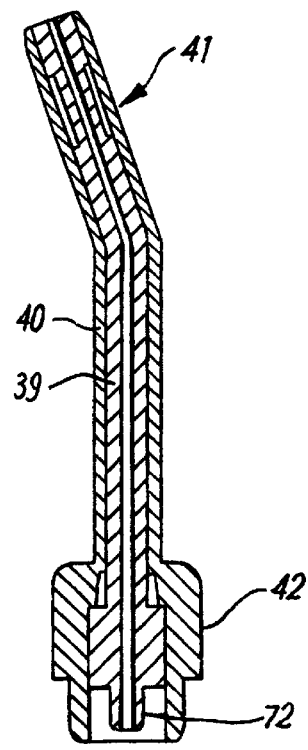

The handpiece is used with a tip as shown in FIGS. 5 and 6 which is connected to the head by the tip connector and valve mechanism 18. This connector and valve mechanism 18 comprises a tubular sleeve structure 25 having forward and rearward coaxial sections 26, 27 respectively of larger and smaller diameter. The larger diameter section 26 has opposed radially inwardly extending bayonet pins 28.

The sleeve structure 25 fits closely within a stepped bore in the head 2 and is sealed relative to the bore by a captive O-ring 29 on the smaller diameter section 27. The structure 25 is free to slide axially through a short distance but is retained relative to the head 2 by an assembly pin 30 pushed transversely through the head and engaging an elongate slot 31 in the smaller diameter section 27.

A spring washer 32 is held captive around the smaller diameter section 27 between a base part of the larger diameter section 26 and a shoulder of the stepped bore in the head 2. The spring washer 32 provides resilient resistance to the axial movement of the sleeve structure 25.

A one way valve mechanism is located axially within and extends through the smaller diameter section 27. This mechanism comprises a cylindrical element 33 with an axial through bore containing a valve ball 34 urged into sealing engagement with a shoulder by means of a helical coil spring 35.

At a rearward end the bore communicates with the cavity 22 connected to the water conduit. The outer surface of the member 33 is sealed relative to this cavity 22 by means of a peripheral O-ring 36.

At a forward end of the member 33 there is an enlarged opening 37 bounded by an O-ring seal 38. There may be a tapered neck within the opening as described in application PCT/GB 98/01754.

There is a gap between the outer surface of the member 33 and the inner surface of the smaller diameter section 27 of the sleeve structure 25. This gap communicates at its rearward end with the cavity 23 connected to the air conduit and at its forward end with the interior of the larger diameter section 27.

Figure 3:
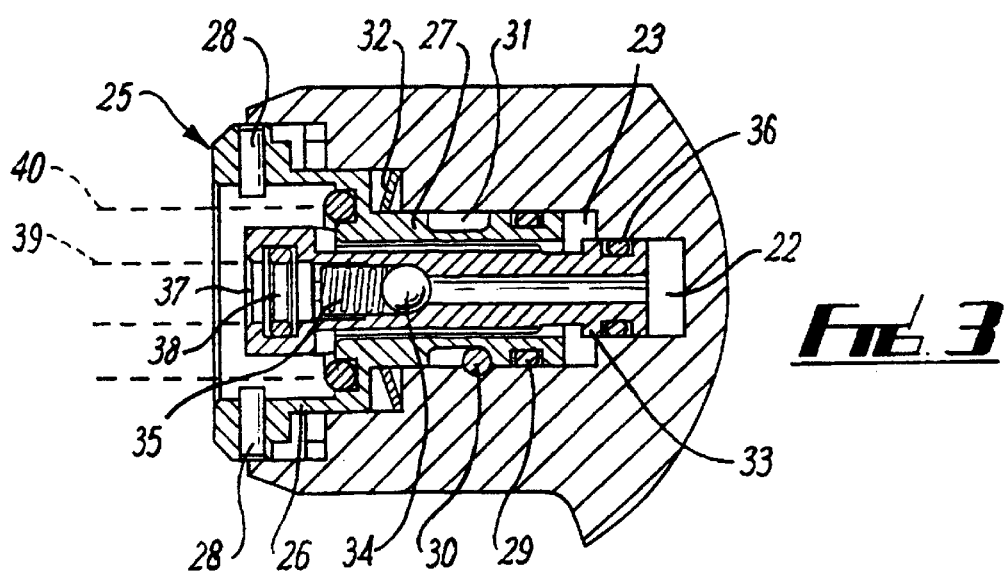
FIGS. 3 & 4 are enlarged details of the handpiece.

The tip, as indicated in broken lines in FIG. 3 and shown in greater detail in FIGS. 5 and 6 has inner and outer coaxially arranged tubes 39, 40. At a forward end the tip has an angled section 41. At a rearward end the tube 40 forms an enlarged outer sleeve 42 through which the inner tube 39 extends. This sleeve part of the tube 40 has opposite side bayonet slots 43. The tip tubes 39, 40 comprise separate plastics mouldings which are united to form a wholly plastics disposable tip structure.

The sleeve part 42 of the tube 40 is inserted into the enlarged diameter section 26 of the structure 25 and the bayonet slots are mated with the bayonet pins 28. The spring washer 32 provides resilience to facilitate pushing in of the tip. The rearward end of the inner tube 39 enters the forward open end 37 of the element 33 and sealingly engages the O-ring 38. A toothed clutch or other mechanism is incorporated in the sleeve structure 25 and the bore in the head so as to lock the sleeve structure relative to the head to prevent rotation of the sleeve structure when it is pushed in against the spring resistance. When the sleeve structure is in its axially outwardly position the sleeve structure 25 and the tip can rotate through 360° relative to the head 2.

In use, water and air can be admitted to the inner and outer tubes 39, 40 of the tip by operating the push buttons 24. Pressurised water flows along the bore in the element 33 and lifts the ball 34 off its shoulder. When flow of water is discontinued, the ball 34 is pressed back on the shoulder to seal the bore and prevent flow back of infected material.

After use the tip can be removed and discarded. After switching off the pressurised air and water at source the body 1 can be unscrewed to allow quick removal of the head 2 which can then be autoclaved for sterilisation purposes. As desired, the sleeve structure 25 and the air and water valve assemblies can be readily removed and disassembled for maintenance.

If desired, the handpiece may include integrated shut off valves to arrest the flow of air and water before the head 2 and body 1 are disengaged.

There may be an actuator which is turned or pulled to operate such shut off valves. Also, instead of the ball 34 other kinds of one way valve arrangement may be used e.g. as described in PCT/GB 98/01754.

Referring now to FIGS. 7 and 8 these show an alternative embodiment.

This embodiment has a head member 44 which screws onto the end of a tubular body member 45 with an intermediate coupling member 46, generally in like manner to the embodiment of FIGS. 1 to 6.

The connector member 46 comprises a cylindrical body which has two through conduits 47, 48 for air and water, such conduits having longitudinally projecting tubular line connectors 49 at a bottom end, and shorter projecting tubular connectors 50 at its top end, bounded by o-ring seals.

The coupling member 46 abuts an internal shoulder of the tubular body member 45, and the two projecting tubular connectors 50 fit tightly into air and water passages within the head member 44 when the body member 45 is screwed fully onto the head member 44.

Air and water lines are pushed onto the line connectors 49 and lead through the tubular body member 45, out of the bottom end, to air and water sources.

The aforesaid air and water passages within the head member 44 connect, via thumb operated shut-off valves 52, like the valves 20 of FIGS. 1 to 6, with forward outlets in the head member 44 yet to be described.

The shut-off valves 52 are inserted into apertures in the head member 44 and are locked in position by an inserted transverse assembly pin 53.

The head member 44 contains a shaped (stepped) socket 54 shown in FIG. 7 and indicated in broken lines in FIG. 8. The innermost bottom end of this socket 54 and a side position on the socket 54 communicate with the aforesaid forward outlets of the air and water passageways in the head member 44.

The innermost (bottom end) region of the socket is therefore essentially the same as the innermost region of the socket in the embodiment of FIGS. 1 to 6.

A connection piece 55 fits within this socket 54 so as to project outwardly therefrom. This piece 55 comprises an outer shaped body 56 generally of circular cross-section throughout, and an inner shaped body 57 also generally of circular cross-section throughout.

The outer body 56 has an enlarged head part 58 at one end, and a narrower extension part 59 projecting centrally at the other end. A forward end of the outer body 56 has a central cylindrical recess 60. A cylindrical through bore 61 extends from the base of this recess 60 through the head part 56 and the extension part 59.

The inner body 57 is generally of the form of a tube with an enlarged head 62 at one end and a through bore 63 which has an enlarged end part within the head 62. This inner body 57 fits securely within the bore 61 of the outer body 56 so that the enlarged head 62 of the inner body 57 is located within the recess 60 and the opposite end 64 is located beyond the extension part 59.

The inner body 57 has external spacers so that a fluid flow passage is defined between the inner body 57 and the outer body 56 along the bore 61.

The enlarged head part 58 of the outer body 56 has diametrically opposed radially inwardly directed bayonet pins 65, and also an o-ring 66 set into the base of the recess 60 around the head 62 of the inner body 57.

The outer body 56 also has an external peripheral o-ring 67 around the extension part 59, and an external peripheral groove 68 between the o-ring 67 and the enlarged head part 58.

The inner body 57 has an inner peripheral o-ring 69 within the enlarged end of the bore 63, and an external peripheral o-ring 70 around the projecting end of the inner body 57.

The connection piece 55 is plugged into the socket 54 so that the o-rings 67, 70 fit tightly within tubular parts of the socket, and most of the enlarged head part 58 projects externally of the head member 44. The connection piece 55 is retained by insertion of another transverse assembly in which engages the groove 68.

In this position, the water and air forward outlets in the head member 44 are in communication with the inner bore 63 and the space between the inner and outer bodies 56, 57 within the bore 61.

The tip, as shown in FIGS. 5 and 6 can now be inserted into the open end of the recess 60 so that the L-shaped bayonet recesses 43 engage the bayonet pins 65, and the inner projection 72 of the tip fits within the enlarged end of the bore 63 within and in sealing contact with the o-ring 69. The tip can be pushed in and twisted, against the resilience of the o-ring 66 to interlock the bayonet recesses 43 and pins 65. The water and air passageways are thereby put into communication with the inner and outer coaxial channels of the tip.

It will be noted that the connection piece 55 is retained within the socket 54 solely by the frictional engagement of the o-rings 67, 70 and the pin 71 which engages the groove 68. This pin 71 prevents removal axially but permits rotation of the connection piece 55. This rotation is advantageous because it facilitates setting of the tip in any angular position suited to particular use requirements. Since this rotation occurs between the connection piece 55 and the head member 44, rather than between the tip and the connection piece 55, secure sealing and firm support of the tip can be more readily assured, i.e. the seal at o-rings 66 and 69 is a static seal.

When desired, the tip can be readily detached, discarded and subsequently replaced. Also, the head member 44 can be readily removed for autoclave sterilisation because the intermediate coupling member 46 provides a quick release facility. That is, after the tubular body 45 has been unscrewed, the head member 44 can be pulled away causing the tubular connection 50 on the coupling member 46 to be removed from the passageways in the head member 44.

The connection piece 55 is an integral part of the handpiece after assembly. That is, the connection piece 55 is secured in position by the assembly pin 71 as part of the process of manufacturing the handpiece and the pin 71, like the pin 53, is not intended or adapted to be removed by the user. When fully assembled the pins 53, 71 are flush with the surfaces of the head member and cannot readily be removed. The assembled handpiece is therefore dedicated for use with the specific intended tip as indicated. Moreover, the socket 54 within the head member 44 is specific to the form of the connection piece 55, it is not intended or adapted for use with any other connection piece or tip.

What is claimed:

1. A dental syringe assembly comprising:
   a handpiece adapted to be connected to sources of air and water; and
   a tip for directing flow of air and water from the handpiece into a patient's mouth, the tip having an enlarged connector cap at a rear end, and the handpiece having a body member and a head member,
   wherein the head member is provided with a sleeve structure and the connector cap of the tip is detachably interengageable with the sleeve structure,
   wherein the head member is connected to the body member so as to be separable therefrom,
   wherein the body member comprises a tubular structure that is releasably connected to the head member and houses a coupling member with conduits to channel the flow of air and water through the body member to passageways in the head member, and
   wherein the head member is held in detachable engagement with the coupling member by the releasable engagement of the tubular structure with the head member.

2. An assembly according to claim 1 characterised in that the tubular structure is releasably connected to the head member by a screw connection.

3. An assembly according to claim 1 characterised in that the handpiece incorporates air and water shut off valves.

4. An assembly according to claim 3 characterised in that the shut off valves are within the head member.

5. An assembly according to claim 1 characterised in that the connector cap is detachably interengageable with the sleeve structure by means of a bayonet fitting.

6. An assembly according to claim 5 characterised in that the bayonet fitting comprises pins on the sleeve structure and shaped slots on the cap.

7. A dental syringe assembly comprising:
   a handpiece adapted to be connected to sources of air and water; and
   a tip for directing flow of air and water from the handpiece into a patient's mouth, the tip having an enlarged connector cap at a rear end, and the handpiece having a body member and a head member,
   wherein the head member is provided with a sleeve structure and the connector cap of the tip is detachably interengageable with the sleeve structure,
   wherein the sleeve structure is provided in a connection piece attached to the head member,
   wherein the tip has inner and outer coaxial passages for the water and air flow, and
   wherein the sleeve structure comprises a central inner bore to communicate with the inner coaxial passage within the cap, and an outer passageway defined by a recess around the inner bore to communicate with the outer coaxial passage within the cap.

8. An assembly according to claim 7, characterised in that the sleeve structure has O-ring seals respectively between the cap and a bottom wall of the recess, and the inner bore and a projection of the inner coaxial passage.

9. A dental syringe assembly comprising:
   a handpiece adapted to be connected to sources of air and water; and
   a tip for directing flow of air and water from the handpiece into a patient's mouth, the tip having an enlarged connector cap at a rear end, and the handpiece having a body member and a head member,
   wherein the head member is provided with a sleeve structure and the connector cap of the tip is detachably interengageable with the sleeve structure,
   wherein the sleeve structure is provided in a connection piece attached to the head member within a socket of the head member, whereby air and water passageways in the head member are in sealed communication respectively with air and water passageways in the connection piece, and wherein the connection piece has projecting innermost structures with peripheral O-rings which engage side walls of the socket to provide said sealed communication.

10. An assembly according to claim 9 characterised in that the connection piece has a head part which projects externally of the head member of the handpiece, the sleeve structure being provided exclusively within this head part.

11. An assembly according to claim 9 characterised in that the connection piece is located within the socket so as to be rotatable about its axis whilst being retained against axial separation.

12. An assembly according to claim 11 characterised in that the connection piece is retained by a transverse assembly pin passed through the head member and engaging a peripheral groove in the connection piece.

13. A handpiece for a dental syringe assembly adapted to be connected to sources of air and water, and to a tip for directing flow of air and water from the handpiece into a patient's mouth, wherein the handpiece is comprised of at least two releasably connectable members comprising a head member which is adapted to be connected to the tip and a body member which is adapted to be connected to the air and water sources, the head member incorporating a non-return valve.

14. A handpiece according to claim 13 characterised in that the body member houses a coupling member with counduits to channel the flow of air and water through the body to the head member.

15. A handpiece according to claim 14 characterised in that the body member comprises a tubular structure releasably engaged relative to the head member.

16. A handpiece according to claim 15 characterised in that the head member is held in detachable engagement with the coupling member by the releasable engagement of the tubular structure with the head member.

17. A handpiece according to claim 13 characterised in that the non-return valve is applied to water delivery.

18. A handpiece according to claim 13 characterised in that the non-return valve has a spring loaded valve member which is urged into sealing engagement with a valve seat, fluid pressure during normal operation being sufficient to move the member off the seat to permit passage of fluid.

19. A handpiece according to claim 13 characterised in that the non-return valve incorporates an outlet flow nozzle to direct flow into the water passage of the tip.

20. A handpiece for a dental syringe assembly adapted to be connected to sources of air and water, and to a tip for directing flow of air and water from the handpiece into a patient's mouth, wherein the handpiece is comprised of at least two releasably connectable members, and incorporates a sleeve structure for detachable engagement with the tip, and wherein said sleeve structure is incorporated in a head member and incorporates a non-return valve.

21. A handpiece according to claim 20 characterised in that the sleeve structure is located in a bore in the handpiece so as to be movable axially inwardly of the handpiece against the action of a spring.

22. A handpiece according to claim 21 characterised in that the sleeve structure, and hence the tip when connected thereto, is rotatable when the sleeve structure is spring urged to an outer limit position.

23. A handpiece according to claim 22 characterised in that a mechanism is provided to resist rotation when the sleeve structure is pushed against the spring to an inner limit position.

24. An assembly of a handpiece according to claim 20 and a tip wherein the tip is connected to the handpiece by a bayonet fitting.

* * * * *